United States Patent
Lee

(10) Patent No.: US 11,744,815 B1
(45) Date of Patent: Sep. 5, 2023

(54) PHARMACEUTICAL COMPOSITION OF DIMETHYLGUANIDINO VALERIC ACID AND PLANT FLAVONOIDS FOR TREATING CHRONIC INFLAMMATORY DISEASES AND CANCER

(71) Applicant: Jongdae Lee, San Diego, CA (US)

(72) Inventor: Jongdae Lee, San Diego, CA (US)

( * ) Notice: Subject to any disclaimer, the term of this patent is extended or adjusted under 35 U.S.C. 154(b) by 0 days.

(21) Appl. No.: 17/663,669

(22) Filed: May 17, 2022

(51) Int. Cl.
- *A61K 31/198* (2006.01)
- *A61K 31/352* (2006.01)
- *A61P 19/02* (2006.01)
- *A61P 35/00* (2006.01)
- *A61P 37/06* (2006.01)

(52) U.S. Cl.
CPC .......... *A61K 31/198* (2013.01); *A61K 31/352* (2013.01); *A61P 19/02* (2018.01); *A61P 35/00* (2018.01); *A61P 37/06* (2018.01)

(58) Field of Classification Search
CPC ..... A61K 31/198; A61K 31/352; A61P 19/02; A61P 35/00; A61P 37/06
See application file for complete search history.

(56) References Cited

PUBLICATIONS

Yang et al (Frontiers in Immunology, 2022, vol. 13, Article 918241 (Year: 2022).*
Ottosson (Journal of the American Heart Association, 2019,vol. 8, Iss. 19 (Year: 2019).*

* cited by examiner

*Primary Examiner* — Susanna Moore
*Assistant Examiner* — Luisalberto Gonzalez

(57) ABSTRACT

The present invention relates to the technical field of disease treatment, and more specifically, it relates to a pharmaceutical composition, having arginine metabolite dimethylguanidino valeric acid (DMGV) or plant flavonoids to treat chronic inflammatory and cancers. Disclosed in the present invention are plant flavonoids including kaempferol, daidzein, and quercetin. Treated chronic inflammatory diseases include rheumatoid arthritis (RA), inflammatory bowel disease (IBD), and cancer further including hematological cancers as well as solid tumor.

4 Claims, 9 Drawing Sheets

PHARMACEUTICAL COMPOSITION OF DIMETHYLGUANIDINO VALERIC ACID AND PLANT FLAVONOIDS FOR TREATING CHRONIC INFLAMMATORY DISEASES AND CANCER

FIELD OF THE INVENTION

The present invention relates to pharmaceutical sector, and more particularly to the composition of the arginine metabolite Dimethylguanidino Valeric Acid (DMGV) or plant flavonoids to treat chronic inflammatory diseases and cancers.

BACKGROUND OF THE INVENTION

T and B cells (lymphocytes) are crucial for effective immunity but uncontrolled activation and subsequent proliferation of lymphocytes are the underlying cause of many autoimmune and/or chronic inflammatory diseases. Similarly, uncontrolled proliferation of any cell type due to genetic mutations can become a cancer. To proliferate fast, both lymphocytes and cancer cells use, as the main source of energy, the metabolic program called Warburg effect in which glycolysis to generate energy and building blocks necessary for daughter cells. We have found that DMGV and the flavonoids induce peroxide anion by activating MCU, which inhibits proliferation of rapidly dividing cells such as lymphocytes and cancer cells. DMGV is generated in the mitochondria when ADMA (asymmetric dimethylarginine) or SDMA (symmetric dimethylarginine) is metabolized by AGXT2 (alanine-glyoxylate aminotransferase 2). Thus, neither ADMA nor SDMA can induce ROS in the absence of AGXT2. Therefore, our discovery is novel and different from the previous one in which ADMA, but not SDMA and DMGV, is an inhibitor of nitric oxide (NO) synthase. In a further proof, a selective inhibitor of inducible nitric oxide (iNOS) inhibitor, N6-(1-iminoethyl)-L-lysine, does not induce ROS or inhibit T cell proliferation, demonstrating that the current invention on ADMA, SDMA and DMGV is not related to NO synthesis.

SUMMARY OF THE INVENTION

In its broadest aspect, the present invention provides a new pharmaceutical composition and mechanism to treat cancer and chronic inflammatory diseases by inhibiting glycolysis with DMGV or flavonoids.

In the first aspect of the invention, it is to provide the application of the arginine metabolite DMGV in the preparation of treating chronic inflammatory diseases and cancers.

In another aspect of the invention, it is to provide the application of flavonoids in the preparation of treating chronic inflammatory diseases and cancers.

The present invention provides the application of the arginine metabolite DMGV in the preparation of treating chronic inflammatory diseases and cancers.

The arginine metabolite DMGV inhibits proliferation of lymphocytes and cancer cells by targeting glycolysis. DMGV is essential for cell survival at the physiological level because T cells without DMGV do not survive after stimulation, but an excess amount of DMGV inhibits cell survival. DMGV generates reactive oxygen species (ROS) in the mitochondria by activating the mitochondrial calcium uniporter (MCU). The mitochondrial ROS induced by DMGV thus controls the cell survival; the physiological level of DMGV is essential for survival while an excessive level of it inhibits cell survival.

It is demonstrated in animal models that DMGV can treat chronic inflammatory diseases, such as rheumatoid arthritis (RA) and inflammatory bowel disease (IBD), and suppresses proliferation of cancer cells.

The invention also provides applications of flavonoids in the preparation of treating chronic inflammatory diseases and/or cancers.

Flavonoids such as kaempferol, daidzein and quercetin, are structurally unrelated to DMGV. Through mechanism study, the invention finds that flavonoid can also induce ROS, which was not known before, and inhibit proliferation of lymphocytes and cancer cells.

It was known that flavonoid also activate MCU, but here we demonstrate that they inhibit proliferation of lymphocytes and cancer cells in the same mechanism as DMGV, by inducing mitochondrial ROS. The invention has no relevance to NO synthesis.

BRIEF DESCRIPTION OF THE DRAWINGS

FIG. 2A shows DMGV suppresses survival of T cells;

FIG. 2B shows DMGV suppresses survival of Jurkat (Human T lymphocytic leukemia cell lines), THP-1 (Acute monocytic leukemia cell lines), HL-60 (Acute myeloid leukemia M3 cell lines) and K-562 (Human chronic myeloid leukemia cell lines) cells;

FIG. 2C shows DMGV suppresses proliferation of HCT-8 (Human colorectal cancer cell lines), HCA-7 (colorectal cancer cell lines) and PC-3 (Human prostate cancer cell lines).

FIG. 3A the identification of human Jurkat T cell and mouse blood cells in the peripheral blood of a mouse. NOD/SCID mice are immune-deficient so that Jurkat cells can proliferate before and after injection of Jurkat cells, mouse blood cells were analyzed by flow cytometry, the cancer-bearing mouse shows 60% of blood cells are Jurkat cells.

FIG. 3B show the schematic drawing of cancer treatment regime.

FIG. 3C shows DMGV completely eliminated Jurkat cells after two-week treatment.

FIG. 3D shows DMGV treatment protects mice from the cancer-induced death.

FIG. 4A shows the dose-dependent induction of mitochondrial ROS (reactive oxygen species) by DMGV in T cells; FIG. 4B confirms DMGV induces ROS generation specifically in the mitochondria;

FIG. 4C shows MitoQ reverses the inhibition of T cell survival rate by DMGV.

FIG. 5A shows DMGV inhibits energy metabolism in mouse T cells as measured by the Seahorse assay;

FIG. 5B shows DMGV no longer affects T cell survival in a glucose-free culture condition;

FIG. 5C shows DMGV does not induce mitochondrial ROS in a glucose-free medium.

FIG. 6A shows the metabolic pathway for DMGV synthesis in cells;

FIG. 6B shows the strategy and proof for generation of AGXT2-KO mice (left) and genetic verification results of AGTX2-KO mice (right), the primer set 1 can only amplify the AGXT2$^{-/-}$ allele while the primer set 2 can only amplify the AGXT2$^{+/+}$ allele;

FIG. 6C shows ADMA (10 μM) and SDMA (10 μM) do not induce ROS in AGXT2$^{-/-}$ T cells but DMGV (504) still does;

FIG. 6D shows MitoQ rescues AGXT2$^{+/+}$ T cells from DMGV-induced inhibition while it inhibits DMGV-induced rescue of AGXT2$^{-/-}$ T cells.

FIG. 7A shows DMGV induces calcium efflux but not influx; FIG. 7B shows DMGV induces calcium influx to the mitochondria and ROS via MCU; FIG. 7C shows TCR-induced calcium flux is independent of MCU.

FIG. 8A shows the flavonoids induce mitochondrial calcium influx and ROS. Jurkat T cells were treated with kaempferol (5 μM), quercetin (25 μM), or daidzein (5 μM); FIG. 8B shows molecular docking program Swissdock predicts DMGV and the flavonoids form hydrogen bond to Isoleucine 127 or/and Valine 135 (Val 135);

FIG. 8C shows DMGV is completely but quercetin is partially dependent on Ile127 while daidzein and kaempferol are independent on it;

FIG. 8D shows DMGV is independent on Val135 while kaempferol is totally dependent on it;

FIG. 8E shows kaempferol suppresses T cell survival via mitochondrial ROS.

FIG. 9A shows DMGV rescues mice from death induced by colonic inflammation; FIG. 9B shows DMGV decreases the number of IL-17A positive T cells in the colons; FIG. 9C shows DMGV suppresses the arthritic symptoms in mice.

DETAILED DESCRIPTION OF THE INVENTION

Definitions

Figure 1:
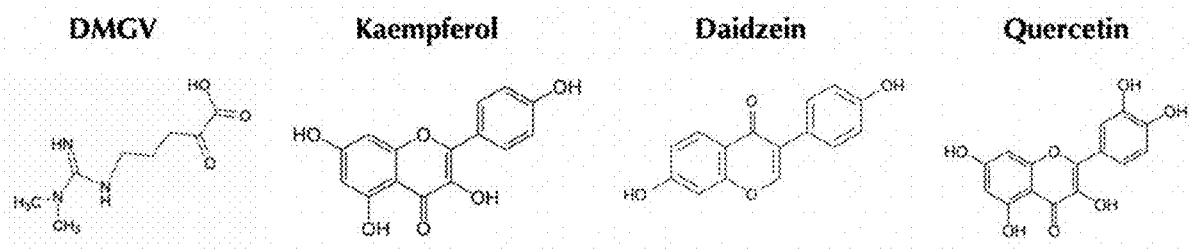
FIG. 1 shows Chemical structures of DMGV and the flavonoids.

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination.

Lymphocyte: The term "lymphocyte" as used herein refers to T cells and B cells.

Proliferation: The term "proliferation" as used herein refers to division of cells.

Inhibit or inhibiting: The term "inhibit or inhibiting" as used herein refers to prohibit or prohibiting from doing something such as proliferation.

Treatment or treating: The term "treatment or treating" as used herein refers to therapeutic treatment wherein the object is to slow down (lessen) if not cure the targeted pathologic condition or disorder or prevent recurrence of the condition.

Inhibitor: The term "inhibitor" as used herein refers to a compound or molecule that blocks a specific function.

Degradation of dimethylarginine: The term "degradation of dimethylarginine" as used herein refers to metabolic decomposition of dimethylarginine.

Abnormal proliferation: The term "abnormal proliferation" as used herein refers to either less or more proliferation than the control cells.

Induce, induction or inducing: The term "induce, induction or inducing" as used herein refers to cause, or causing.

DMGV: Chemical name is dimethylguanidino valeric acid.

Kaempferol: Chemical name is
3,5,7-Trihydroxy-2-(4-hydroxyphenyl)-4H-chromen-4-one Daidzein: Chemical name is 7-hydroxy-3-(4-hydroxyphenyl)-4H-chromen-4-one Quercetin: Chemical name is
2-(3,4-Dihydroxyphenyl)-5,7-dihydroxy-4H-1-benzopyran-4-one Throughout, various aspects of the invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 5 should be considered to have specifically disclosed sub-ranges such as from 1 to 3, from 1 to 4, from 2 to 4, from 3 to 5 etc., as well as individual numbers within that range, for example, 1, 2, 3, 4, and 5. This applies regardless of the breadth of the range.

Other objects, advantages and features of the present invention will become apparent from the following specification taken in conjunction with the accompanying drawings.

EXAMPLES

Example 1. DMGV Inhibits Proliferation of "T Cells" and Tumor Cells

Figure 2:
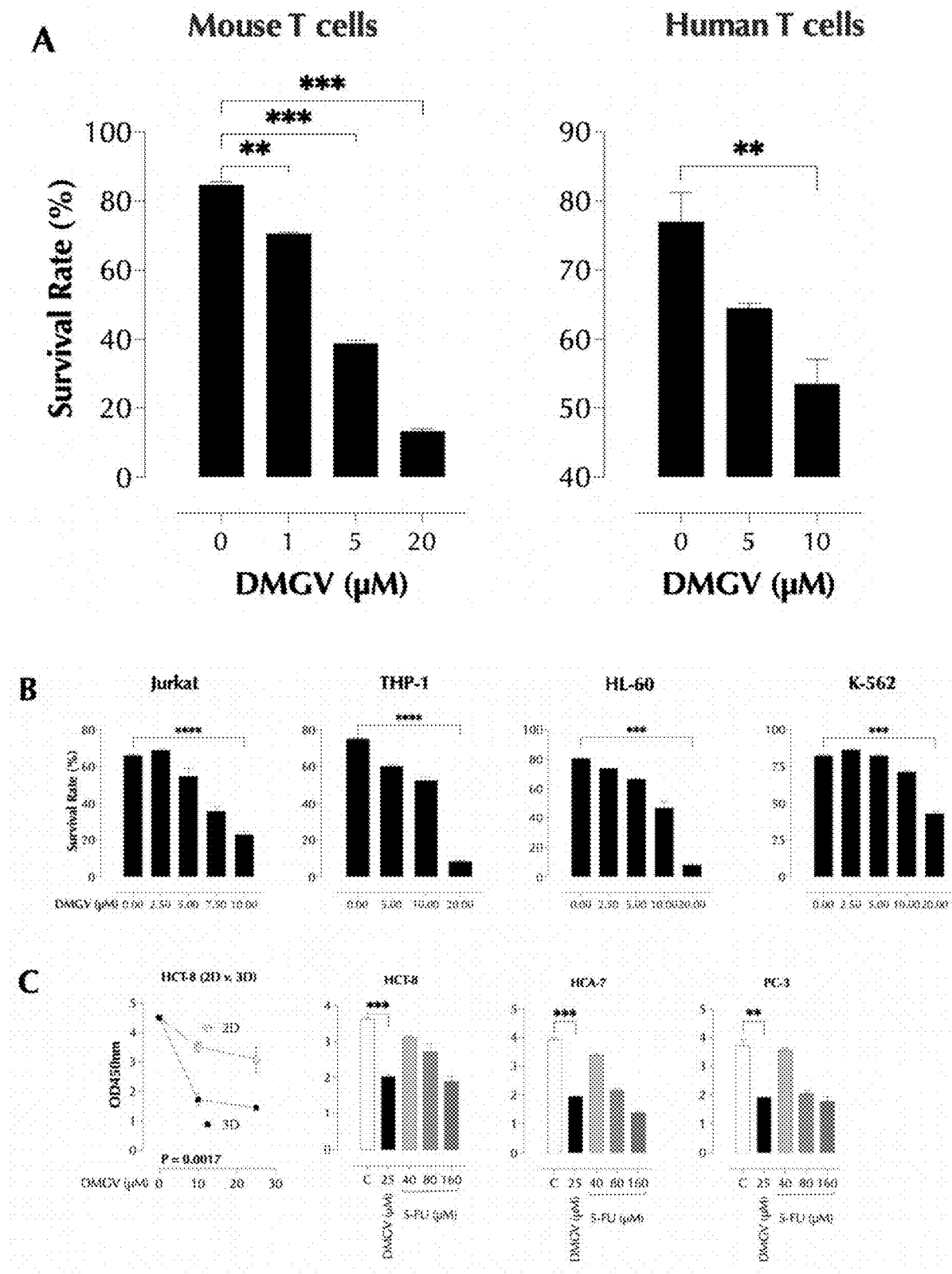
FIG. 2 shows the inhibitory effect of DMGV on T cells and cancer cell proliferation.

In example one, pharmaceutical composition was screened and discovered natural small molecules that inhibit T cell survival and proliferation to use as therapeutics for chronic inflammatory diseases and cancers as taught in FIG. 1, T cells were stimulated with or without the indicated amount of DMGV and survival was measured by flow cytometry after 3 days. DMGV was found to inhibit the survival and proliferation of activated T cells, and the inhibitory effect is proportional to the dose according to FIG. 2A, DMGV also inhibited the survival of hematological cancer cell lines as in FIG. 2B. For solid cancer cells, the invention tested DMGV on the colorectal carcinoma HCT-8 in two different conditions (2D, 2-dimensional culture vs. 3D, 3-dimensional culture), and found that DMGV was much more effective in suppressing proliferation of HCT-8 cultured in Matrigel™ (3D) than 2D. Solid tumor cancer cell lines were incubated with different doses of DMGV or 5-FU (5-fluorouracil), and cells survival was measured by CCK-8 after 2 days. These data demonstrated that DMGV inhibited proliferation of HCT-8 better than a known chemotherapeutic drug, 5-FU (FIG. 2C).

Example 2. DMGV Cures T Cell Leukemia in Mice and Protects Mice from Death

Figure 3:
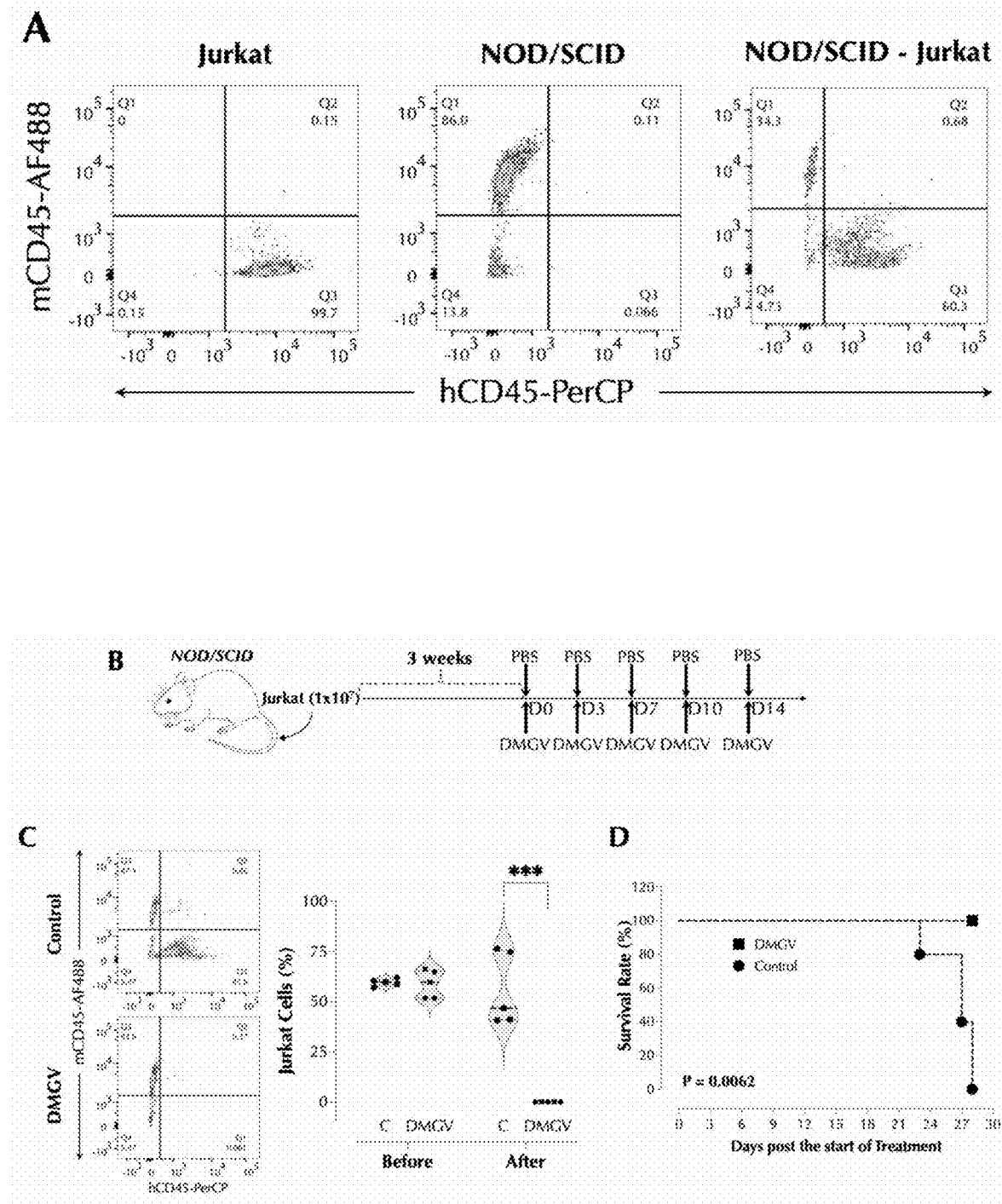
FIG. 3 shows DMGV cures T cell lymphoma in mice.

The next experiment tested whether DMGV can eliminate cancer cells in vivo. We established the T cell leukemia model by injecting Jurkat cells ($1 \times 10^7$) into the tail vein of NSG/SCID mice as seen in FIG. 3A. After 2 weeks of the injection, the level of Jurkat cells in the peripheral blood reached around 60% of the total leukocytes. The model mice were injected with either PBS (Control) or DMGV (700 µg/mouse intraperitoneal injection, i.p.) for 2 weeks as shown in FIG. 3B. DMGV completely eliminated Jurkat cells after 2 weeks of treatment (FIG. 3C) and prevented the cancer-induced death after 4 weeks of treatment FIG. 3D.

Example 3. DMGV Induces ROS in the Mitochondria

Figure 4:
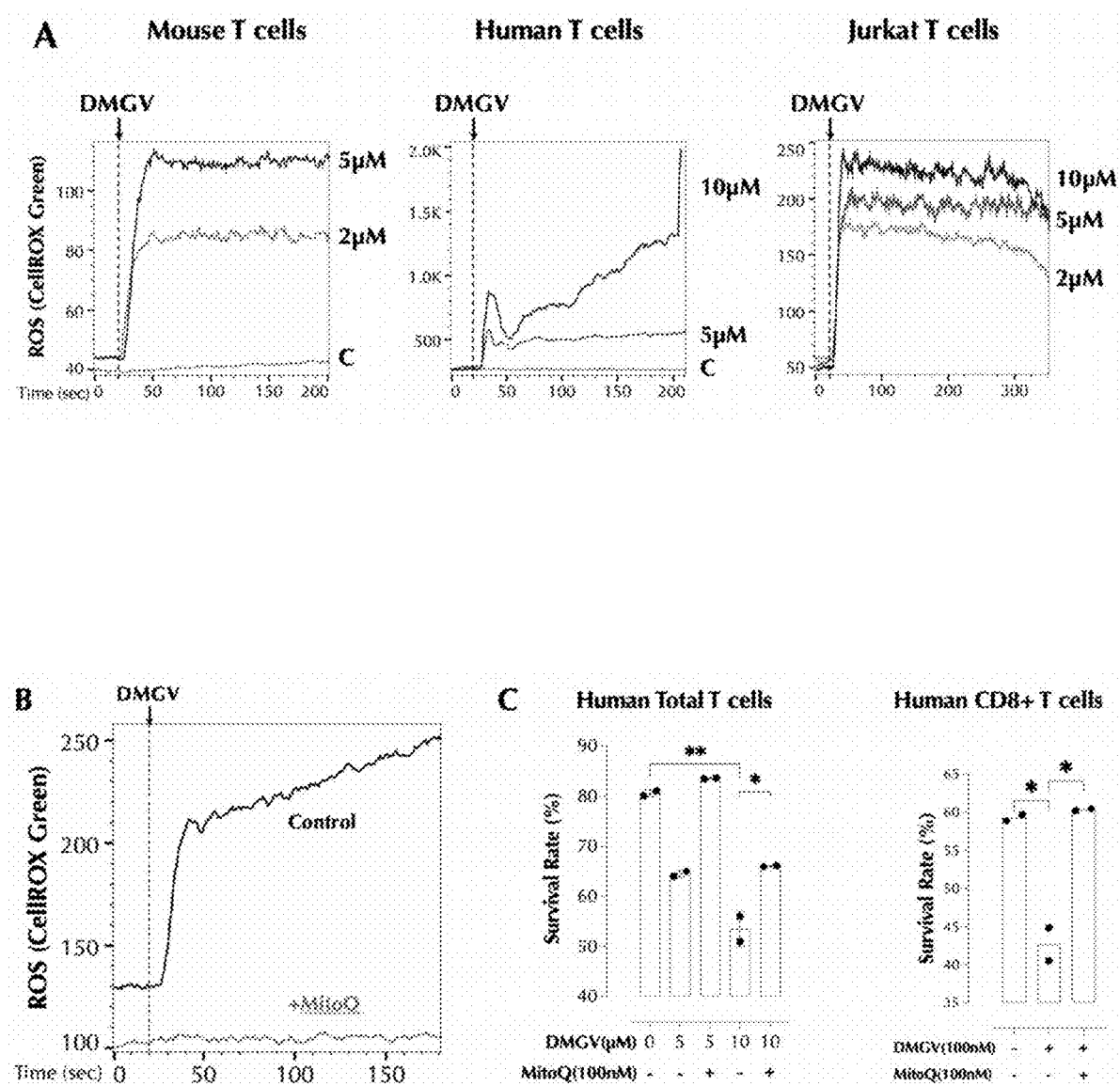
FIG. 4 shows DMGV induces ROS in the mitochondria.

The invention further investigated how DMGV suppresses cell proliferation and survival. We found that DMGV rapidly induces mitochondrial ROS in mouse, human, and Jurkat T cells as taught in FIG. 4A and the induction of mitochondrial ROS by DMGV in T cells was measured by flow cytometry using CellROX Green™.

In order to locate the cellular compartment of ROS generated by DMGV, Jurkat T cells were incubated with the mitochondria-specific ROS inhibitor MitoQ (100 nM) for 15 min before stimulation with DMGV (504) for ROS measurement. Although CellROX Green™ is a mitochondria-specific ROS indicator, we further confirmed the specificity of mitochondrial ROS induction by DMGV since MitoQ completely inhibited ROS production as in FIG. 4B.

In order to test whether DMGV inhibits T cell proliferation by generation of mitochondrial ROS, human T cells were stimulated with or without the indicated amount of DMGV (with or without MitoQ) for 4 days and the survival rates were measured by flow cytometry, MitoQ rescued T cells from DMGV-induced cell death. In summary, the experimental data show that DMGV inhibits T cell survival by specifically inducing mitochondrial ROS production according to FIG. 4C.

Example 4: DMGV Suppresses Cell Survival by Inhibiting Glycolysis

The invention tested if DMGV relied on glycolysis to suppress cell survival. DMGV significantly inhibited both glycolysis and oxidative phosphorylation in activated T cells as seen in FIG. 5A.

In order to test the effects of glycolysis on the DMGV function to inhibit survival, mouse T cells were activated with or without DMGV in RPMI with or without glucose for 4 days and the survival rates were measured by flow cytometry. It was found that DMGV no longer affected T cell survival in a glucose-free culture condition FIG. 5B. Oxidative phosphorylation uses pyruvate, an end product of glycolysis, and thus a diminished glycolysis can decrease oxidative phosphorylation. Supplementation of pyruvate (2 mM) also overcame DMGV-induced effect on T cell survival in a glucose-containing medium (data not shown).

Figure 5:
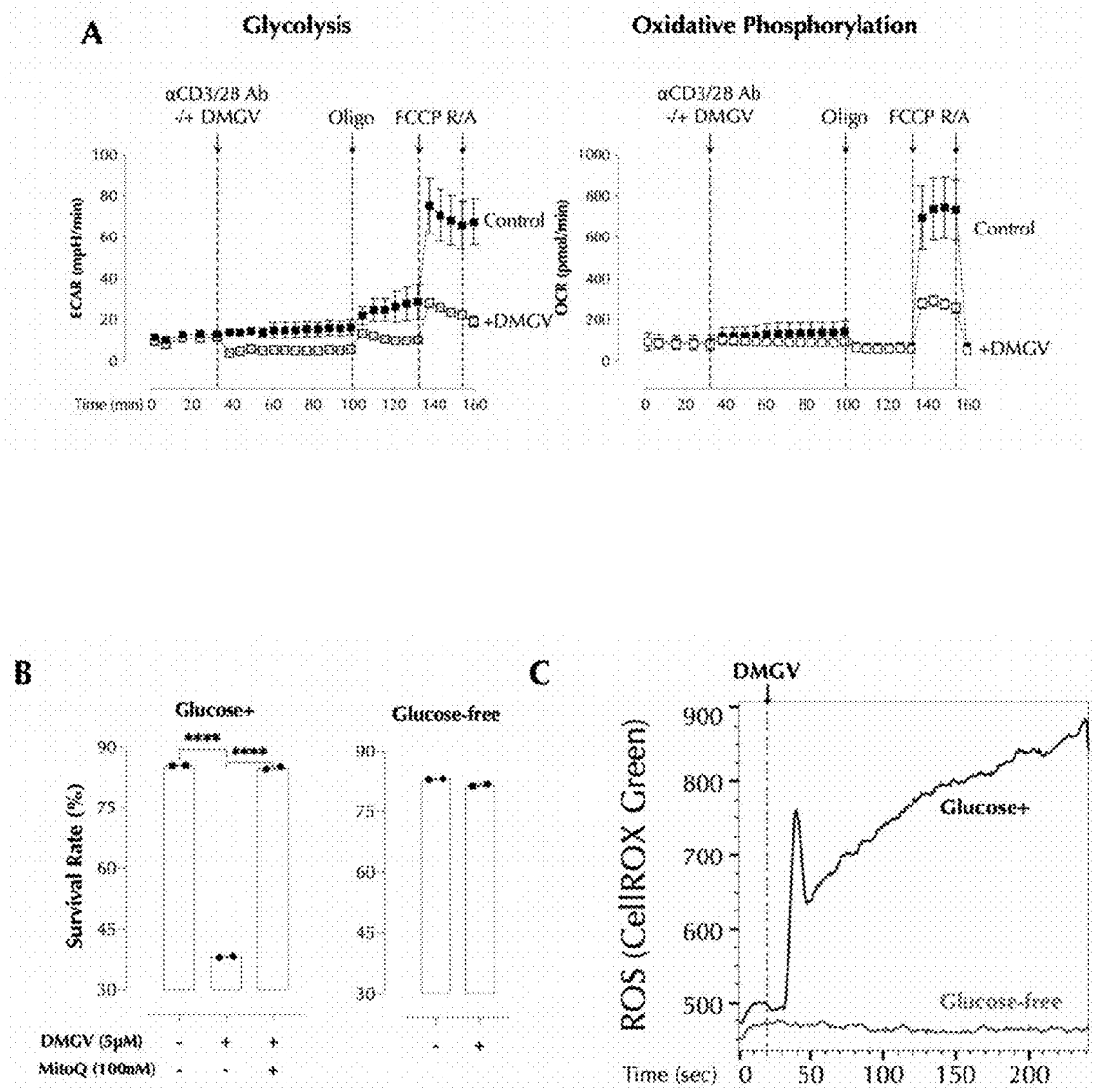
FIG. 5 shows that DMGV suppresses T cell survival by inhibiting glycolysis-dependent ROS.

In addition, DMGV does not induce ROS in a glucose-free medium in Jurkat T cells that were incubated in RPMI without glucose for 24 h according to FIG. 5C. These data indicate that glycolysis is essential for DMGV to induce ROS and suppress T cell survival.

These data indicate that DMGV inhibits cell survival by inhibiting glycolysis and also that it generates ROS in a glycolysis-dependent manner.

Example 5: Physiological DMGV is Essential for T Cell Survival

Figure 6:
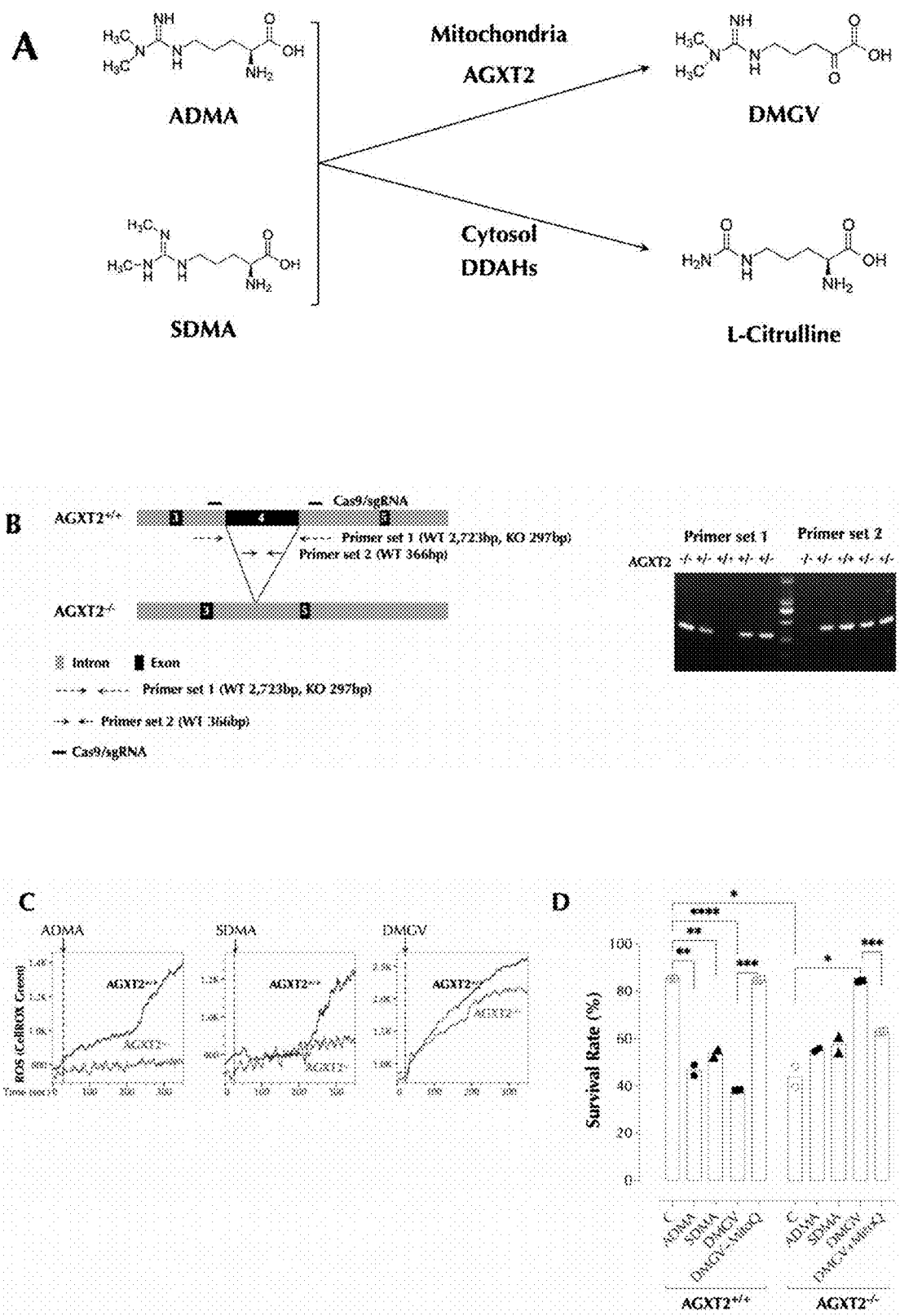
FIG. 6 shows DMGV is a "rheostat" of T cell survival.

DMGV is converted from asymmetric dimethylarginine (ADMA) or symmetric dimethylarginine (SDMA) by alanine-glyoxylate aminotransferase 2 (AGXT2) in the mitochondria whereas ADMA or SDMA is metabolized to L-citrulline in the cytosol as shown in FIG. 6A. In order to investigate the role of DMGV in T cells, we generated AGXT2-KO (AGXT2$^{-/-}$) mice using Crispr/Cas9 technology according to FIG. 6B. Neither ADMA (10 µM) or SDMA (10 µM) induce ROS in AGXT2$^{-/-}$ T cells but DMGV (504) still does, an evidence that SDMA or ADMA induces ROS only when they are converted to DMGV (FIG. 6C).

To investigate the role of AGXT2 and DMGV in T cell survival, AGXT2$^{+/+}$ and AGXT2$^{-/-}$ T cells were stimulated with the indicated compounds (ADMA: 10 µM, SDMA: 10 µM, DMGV: 504, MitoQ: 100 nM) for 4 days and the survival rate was measured by flow cytometry. Unexpectedly, survival of AGXT2$^{-/-}$ T cells was significantly diminished (FIG. 5D). Furthermore, while DMGV inhibited survival of AGXT2$^{+/+}$ T cells, it rescued AGXT2$^{-/-}$ T cells (FIG. 6D). Consistently, MitoQ rescued AGXT2$^{+/+}$ T cells from DMGV-induced inhibition while it inhibited DMGV-induced rescue of AGXT2$^{-/-}$ T cells as shown in FIG. 5D. These data demonstrate that the cell intrinsic level of DMGV is essential for survival as manifested in AGXT2T cells but the excess amount of DMGV is toxic to T cells, making DMGV a "rheostat" of T cell survival.

Example 6: DMGV Activates MCU to Induce ROS

Figure 7:
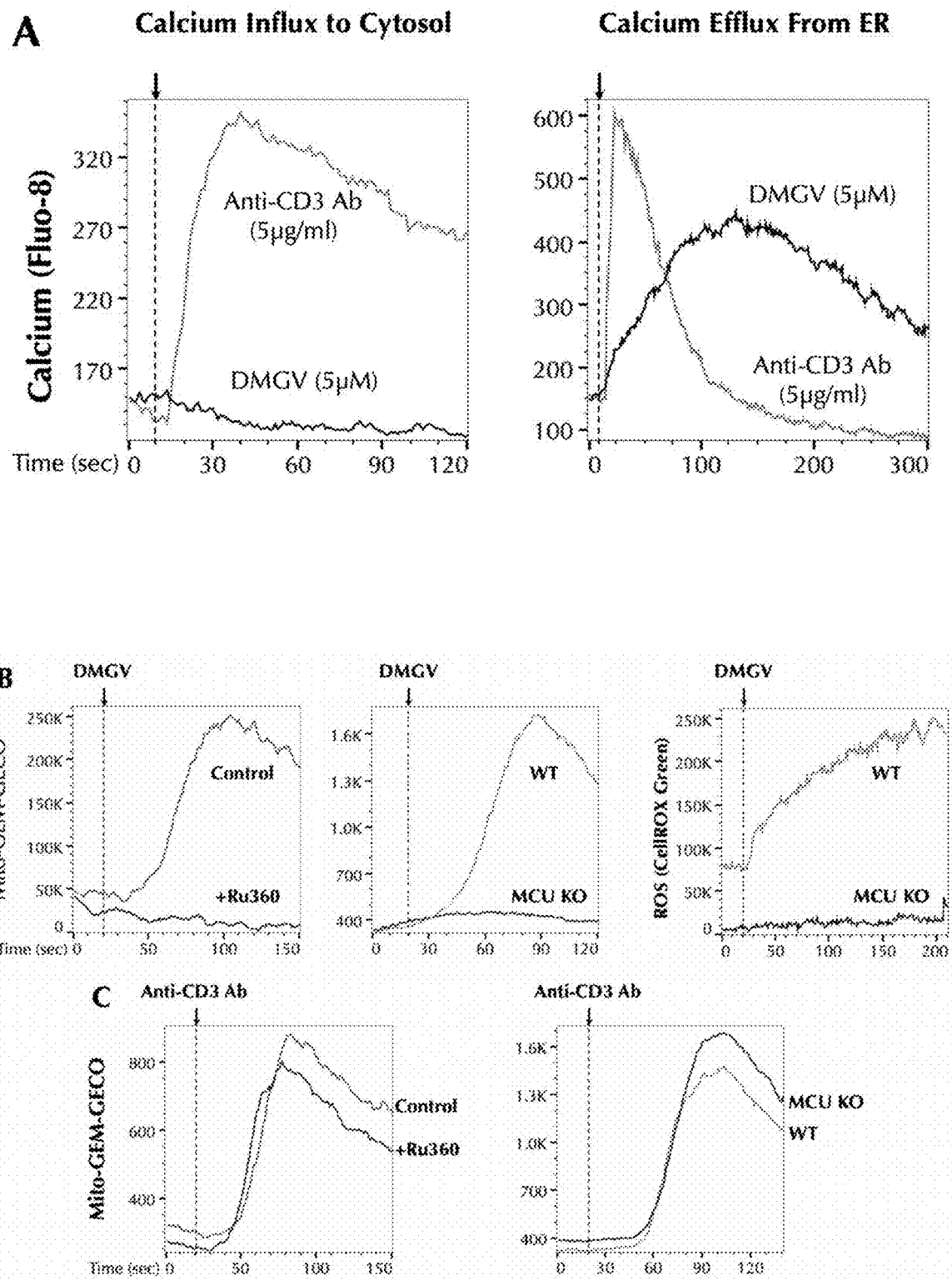
FIG. 7 shows DMGV induces ROS via MCU.

As a sudden influx of calcium to the mitochondria can cause ROS induction, we tested whether DMGV regulates calcium flux to induce ROS. Calcium flux was measured by flow cytometry using the calcium indicator Fluo-8. While stimulation of T cell receptor (TCR) by a stimulatory antibody triggered calcium release from ER (efflux), which in turn induced calcium influx from the outside to cytosol (influx). However, DMGV induced efflux but not influx as in FIG. 7A. Because of the close proximity between ER and mitochondria, calcium efflux from ER leads to calcium import to the mitochondria, which can be mediated by MCU. To test whether DMGV induces calcium influx to the mitochondria, we used the specific MCU inhibitor Ru360 and MCU knockout (KO) cells (Jurkat cells expressing the mitochondrial calcium indicator Mito-GEM-GECO were treated with or without the MCU inhibitor Ru360 (104). And MCU was knocked out by Crispr/Cas9). As expected, the DMGV-induced calcium influx to the mitochondria was completely inhibited by Ru360 or MCU KO according to FIG. 7B.

In addition, DMGV-induced ROS was also dependent on MCU as taught in FIG. 6B, indicating that DMGV-induced calcium influx via MCU to the mitochondria is responsible for ROS production. However, TCR-induced calcium flux was not affected by Ru360 or MCU KO according to FIG. 7C, demonstrating that TCR uses a different mitochondrial calcium channel.

Example 7 DMGV Binds to MCU Via a Hydrogen Bond to Isoleucine 127

Figure 8:
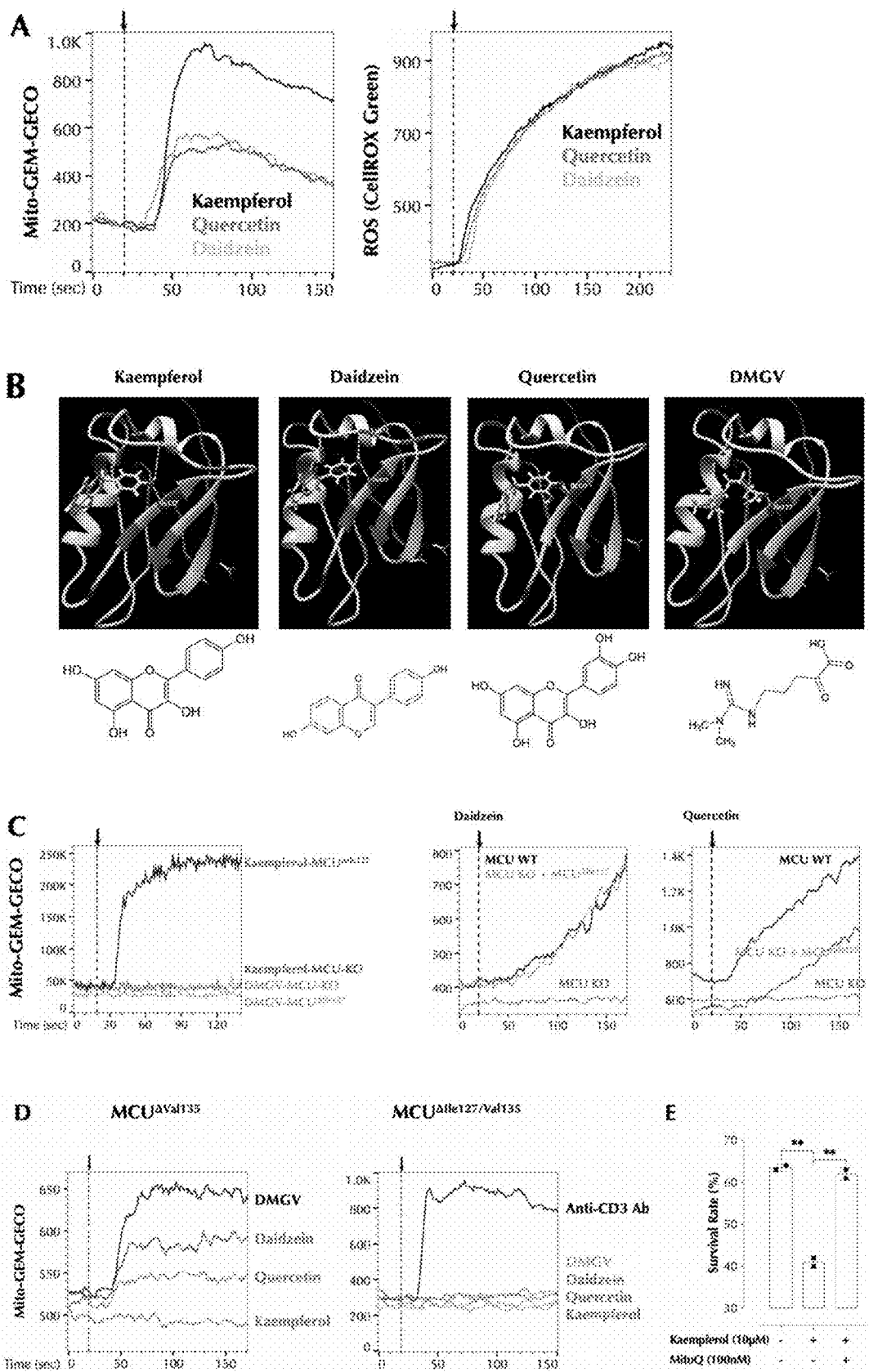
FIG. 8 shows DMGV forms a hydrogen bond to Isoleucine 127 (Ile127) in MCU in silico.

As certain flavonoids are known to active MCU, we tested whether DMGV and the flavonoids activate MCU in the same manner. Jurkat T cells were treated with the flavonoids [kaempferol (5 µM), quercetin (25 µM), or daidzein (5 µM)]. The results indicate that all 3 induced mitochondrial calcium as wells ROS as demonstrated in FIG. 8A. The molecular docking simulator SwissDock predicted that the flavonoids and DMGV bind to MCU in a same pocket. Kaempferol and daidzein were predicted to form two hydrogen bonds with MCU, one to Isoleucine127 and another to Valine135, but quercetin and DMGV with a single hydrogen bond to Ile127 (FIG. 8B).

To test whether Ile127 and V135 are important for these compounds to activate MCU, we generated 3 different MCU mutants deleted of Ile127, V135, or Ile127 and V135. These MCU mutants were transfected to MCU KO cells and stimulated with kaempferol, daidzein, quercetin, or DMGV. DMGV and quercetin were dependent mostly on Ile127, while kaempferol and daidzein were mostly dependent on V135 as shown in FIG. 8C and FIG. 8D. Kaempferol also suppressed survival of activated human T cells via mitochondrial ROS according to FIG. 8E. These data demonstrate that MCU activators in general induce mitochondrial ROS to inhibit highly proliferative cells such as activated lymphocytes and cancer cells.

Example 8: DMGV Inhibits Chronic Inflammation by Suppressing Inflammatory Effector T Cells in Mice The present invention tested if DMGV suppresses chronic T cell-mediated inflammation in two mouse models. In the first model, adoptive transfer of naïve $CD4^+$ T cells from syngeneic mice into immunodeficient ($Rag2^{-/-}$) mice induces chronic colitis similar to inflammatory bowel diseases (IBD) in humans, due to differentiation of T cells into pathogenic Th17 cells in the absence of regulatory T cells (Tregs). After adoptively transferring naïve $CD4^+$ T cells from syngeneic mice to recombinase activating gene-2-deficient ($Rag2^{-/-}$) mice to induce colitis, the mice showing the disease symptom in the form of loose stool around 4-6 weeks were randomly divided into two groups. One group (n=9) was treated with DMGV (i.p. 750 µg/mouse, twice a week) and the control group (n=11) with PBS up to 40 days and mortality was observed.

Figure 9:
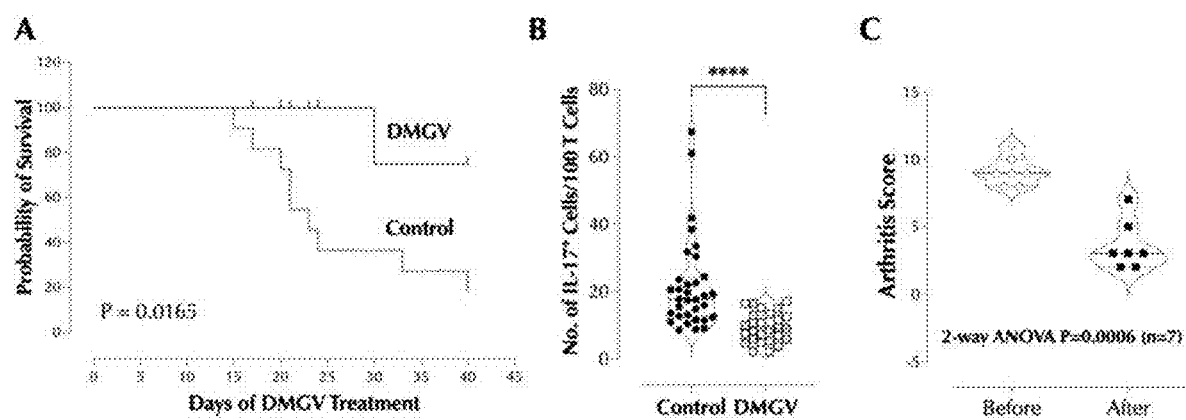
FIG. 9 shows DMGV inhibits chronic inflammation in mice.

At the end of the treatment, all but 2 mice died in the control group whereas all except for one mouse survived in the DMGV-treated group as in FIG. 9A. Colonic tissues of 2 survived mice from each group were frozen, sectioned, and stained for CD3 and IL-17A, the normalized $IL-17A^+$ T cell number in the survived mice was significantly lower in the DMGV treatment group compared to the control group as in FIG. 9B.

In the second model, SKG mice harbor a point mutation in $ZAP-70^{W163C}$ and Develop Chronic autoimmune arthritis similar to human RA due to aberrant T cell activation. The disease can be accelerated by injection of 0-glucan. Laminarian ((3-glucan, 30 mg/mouse) was administered i.p. to SKG mice, and the treatment with DMGV (i.p. 750 µg/mouse, twice a week) began with any mouse reaching the threshold arthritis score of 8, a severe disease. The treatment with DMGV up to 50 days significantly decreased the arthritis score in all treated mice as in FIG. 9C.

Taken together, we have demonstrated that exogenous DMGV suppresses survival of rapidly proliferating cells such as lymphocytes and cancer cells by generating ROS in the mitochondria via MCU. Since other MCU activating compounds such as kaempferol, daidzein, and quercetin also inhibit cell survival by the same mechanism, they can be useful to treat cancers and inflammatory diseases. Our discovery is unrelated to the previous knowledge on ADMA inhibiting NO synthesis.

INDUSTRIAL APPLICATION

The present invention applies to pharmaceutical industry. The invention introduces application of the arginine metabolite DMGV or plant flavonoids to treat chronic inflammatory diseases and cancers.

What is claimed is:

1. A method for inhibiting the proliferation of cancer cells comprising contacting the cancer cells with an inhibitory composition comprising dimethylguanidino valeric acid (DMGV), wherein the cancer cell is selected from Jurkat, THP-1, HL-60, K-562, HCT-8, HCA-7 or PC-3 cancer cells.

2. The method according to claim 1, wherein proliferation is inhibited by activating mitochondrial calcium uniporter (MCU) thereby inducing peroxide anion in the mitochondria.

3. A method for treating cancer comprising administering to a subject in need thereof a pharmaceutical composition comprising dimethylguanidino valeric acid (DMGV), wherein the cancer is selected from colon cancer, rectal cancer, prostate cancer or leukemia.

4. The method according to claim 3, wherein the pharmaceutical composition is administered via an intravenous, subcutaneous, or intramuscular route.

* * * * *